(12) United States Patent
Balko et al.

(10) Patent No.: US 7,291,580 B2
(45) Date of Patent: Nov. 6, 2007

(54) 6-(1,1-DIFLUOROALKYL)-4-AMINO-PICOLINATES AND THEIR USE AS HERBICIDES

(75) Inventors: Terry William Balko, Greenfield, IN (US); Stephen Craig Fields, Indianapolis, IN (US); Nicholas Martin Irvine, Westfield, IN (US); Christian Thomas Lowe, Westfield, IN (US); Paul Richard Schmitzer, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 477 days.

(21) Appl. No.: 10/911,683

(22) Filed: Aug. 4, 2004

(65) Prior Publication Data
US 2005/0032651 A1 Feb. 10, 2005

(51) Int. Cl.
*A01N 43/40* (2006.01)
*C07D 213/79* (2006.01)
*C07D 213/64* (2006.01)
*C07D 409/00* (2006.01)

(52) U.S. Cl. ............ 504/244; 504/255; 504/260; 546/263; 546/261; 546/281.4; 546/284.1

(58) Field of Classification Search ............ 546/281.4, 546/284.1, 289.1, 263, 266.7; 504/244, 255, 504/268
See application file for complete search history.

(56) References Cited

U.S. PATENT DOCUMENTS

| | | | |
|---|---|---|---|
| 3,234,229 A | 2/1966 | Redemann | 260/296 |
| 3,285,925 A | 11/1966 | Johnston et al. | 260/294.9 |
| 3,317,549 A | 5/1967 | Johnston | 260/294.9 |
| 3,325,272 A | 6/1967 | Hamaker et al. | 71/2.5 |
| 3,334,108 A | 8/1967 | Johnston | 260/294.8 |
| 3,755,338 A | 8/1973 | Gulbenk | 260/295 |
| 5,783,522 A | 7/1998 | Schaefer et al. | 504/294 |
| 5,958,837 A | 9/1999 | Schaefer et al. | 504/244 |
| 6,077,650 A | 6/2000 | Price | 430/461 |
| 6,297,197 B1 | 10/2001 | Fields et al. | 504/260 |

FOREIGN PATENT DOCUMENTS

| | | | |
|---|---|---|---|
| BE | 788756 | | 3/1973 |
| EP | 972765 | | 1/2000 |
| WO | 98/21199 | | 5/1998 |
| WO | WO 01/51684 | * | 7/2001 |
| WO | 03/011853 | | 2/2003 |

OTHER PUBLICATIONS

U.S. Appl. No. 10/816,611, filed Apr. 2004, Balko et al.
Ramanand, et al, Reductive Dechlorination of the Nitrogen Heterocycli Herbicide Picloram, *Applied and Environmental Microbiology*, vol. 59, No. 7, Jul. 1993; pp. 2251-2256.

* cited by examiner

*Primary Examiner*—Thomas Mckenzie
*Assistant Examiner*—Raymond Covington
(74) *Attorney, Agent, or Firm*—Craig Mixan

(57) ABSTRACT

4-Aminopicolinic acids having (1,1-difluoroalkyl) substituents in the 6-position and their amine and acid derivatives are potent herbicides demonstrating a broad spectrum of weed control.

6 Claims, No Drawings

6-(1,1-DIFLUOROALKYL)-4-AMINO-PICOLINATES AND THEIR USE AS HERBICIDES

BACKGROUND OF THE INVENTION

This invention relates to certain novel 6-(1,1-difluoroalkyl)-4-aminopicolinates and their derivatives and to the use of these compounds as herbicides.

A number of picolinic acids and their pesticidal properties have been described in the art. For example, U.S. Pat. No. 3,285,925 discloses 4-amino-3,5,6-trichloropicolinic acid derivatives and their use as plant growth control agents and herbicides. U.S. Pat. No. 3,325,272 discloses 4-amino-3,5-dichloro-picolinic acid derivatives and their use for the control of plant growth. U.S. Pat. No. 3,317,549 discloses 3,6-dichloropicolinic acid derivatives and their use as plant growth control agents. U.S. Pat. No. 3,334,108 discloses chlorinated dithio-picolinic acid derivatives and their use as parasiticides. U.S. Pat. No. 3,234,229 discloses 4-amino-polychloro-2-trichloromethylpyridines and their use as herbicides. U.S. Pat. No. 3,755,338 discloses 4-amino-3,5-dichloro-6-bromo-picolinates as fungicides. Belgian patent 788 756 discloses 6-alkyl-4-amino-3,5-dihalopicolinic acids as herbicides. In *Applied and Environmental Microbiology*, Vol. 59, No. 7, July 1993, pp. 2251-2256, 4-amino-3,6-dichloropicolinic acid is identified as a product of the anaerobic degradation of 4-amino-3,5,6-trichloro-picolinic acid, the commercially available herbicide picloram. More recently, U.S. Pat. No. 6,297,197 B1 describes certain 4-aminopicolinates and their use as herbicides. U.S. Pat. No. 5,783,522 discloses certain 6-phenyl picolinic acids and their use as herbicides, desiccants and defoliating agents. WO 0311853 describes certain 6-aryl-4-aminopicolinates and their use as herbicides. WO 9821199 discloses 6-pyrazolylpyridines and their use as herbicides. U.S. Pat. No. 5,958,837 discloses the synthesis of 6-arylpicolinic acids and their use as herbicides, desiccants and defoliating agents. U.S. Pat. No. 6,077,650 discloses the use of 6-phenylpicolinic acids as photographic bleaching agents, and European Patent EP 0 972 765 A1 discloses the synthesis of 2-, 3- or 4-arylpyridines.

SUMMARY OF THE INVENTION

It has now been found that certain 6-(1,1-difluoroalkyl)-4-amino-picolinic acids and their derivatives are potent herbicides with a broad spectrum of weed control against woody plants, grasses and sedges as well as broadleafs and with excellent crop selectivity. The invention includes compounds of Formula I:

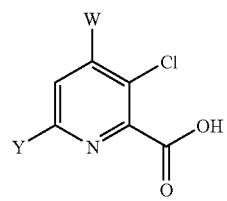

I wherein
Y represents —$CF_2(C_1$-$C_3$ alkyl); and
W represents —$NO_2$, —$N_3$, —$NR_1R_2$, —$N=CR_3R_4$ or —$NHN=CR_3R_4$ wherein
$R_1$ and $R_2$ independently represent H, $C_1$-$C_6$ alkyl, $C_3$-$C_6$ alkenyl, $C_3$-$C_6$ alkynyl, aryl, heteroaryl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl or $C_1$-$C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1$-$C_6$ alkyl, $C_3$-$C_6$ alkenyl, $C_3$-$C_6$ alkynyl, aryl or heteroaryl or $R_3$ and $R_4$ taken together with =C represent a 5- or 6-membered saturated ring; and agriculturally acceptable derivatives of the carboxylic acid group or the 4-amino group.

Compounds of Formula I wherein Y represents —$CF_2CH_3$, and wherein W represents —$NR_1R_2$ and $R_1$ and $R_2$ represent H or $C_1$-$C_6$ alkyl, are independently preferred.

The invention includes herbicidal compositions comprising a herbicidally effective amount of a compound of Formula I and agriculturally acceptable derivatives of the carboxylic acid group or the 4-amino group in admixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation.

DETAILED DESCRIPTION OF THE INVENTION

The herbicidal compounds of the present invention are derivatives of 4-aminopicolinic acids of Formula II:

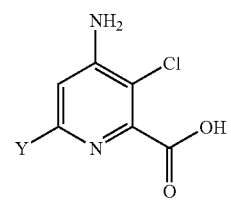

II

These compounds are characterized by possessing Cl in the 3-position and by possessing —$CF_2(C_1$-$C_3$ alkyl) substituents in the 6-position with —$CF_2CH_3$ being preferred.

The amino group at the 4-position can be unsubstituted or substituted with one or more $C_1$-$C_6$ alkyl, $C_3$-$C_6$ alkenyl, $C_3$-$C_6$ alkynyl, aryl, heteroaryl, hydroxy, $C_1$-$C_6$ alkoxy or amino substituents. The amino group can be further derivatized as an amide, a carbamate, a urea, a sulfonamide, a silylamine, a phosphoramidate, an imine or a hydrazone. Such derivatives are capable of breaking down into the amine. An unsubstituted amino group or one substituted with one or two alkyl substituents is preferred.

The carboxylic acids of Formula I are believed to be the compounds that actually kill or control undesirable vegetation and are typically preferred. Analogs of these compounds in which the acid group of the picolinic acid is derivatized to form a related substituent that can be transformed within plants or the environment to a acid group possess essentially the same herbicidal effect and are within the scope of the invention. Therefore, an "agriculturally acceptable derivative", when used to describe the carboxylic acid functionality at the 2-position, is defined as any salt, ester, acylhydrazide, imidate, thioimidate, amidine, amide, orthoester, acylcyanide, acyl halide, thioester, thionoester, dithioester, nitrile or any other acid derivative well known in the art which (a) does not substantially affect the herbicidal activity of the active ingredient, i.e., the 6-(1,1-difluoroalkyl)-4-aminopicolinic acid, and (b) is or can be hydrolyzed, oxidized or metabolized in plants or soil to the picolinic acid of Formula I that, depending upon the pH, is in the dissociated or the undissociated form. The preferred agriculturally acceptable derivatives of the carboxylic acid are agriculturally acceptable salts, esters and amides. Likewise, an "agriculturally acceptable derivative", when used to describe the amine functionality at the 4-position, is defined as any salt, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 6-(1,1-difluoroalkyl)-4-aminopicolinic acid, and (b) is or can be hydrolyzed in plants or soil to a free amine of Formula II. N-Oxides which are also capable of breaking into the parent pyridine of Formula II are also covered by the scope of this invention.

Suitable salts include those derived from alkali or alkaline earth metals and those derived from ammonia and amines. Preferred cations include sodium, potassium, magnesium, and aminium cations of the formula:

$R_5R_6R_7NH^+$ wherein $R_5$, $R_6$, and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethyl-amine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst.

Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecyl-amine, benzylamine or cyclic or aromatic amines with or without additional heteroatoms such as but not limited to aziridine, azetidine, pyrrolidine, pyrrole, imidazole, tetrazole or morpholine. Amides can be prepared by reacting the corresponding picolinic acid chloride, mixed anhydride, or carboxylic ester of Formula I with ammonia or an appropriate amine.

The terms "alkyl", "alkenyl" and "alkynyl", as well as derivative terms such as "alkoxy", "acyl", "alkylthio" and "alkylsulfonyl", as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl", as well as derivative terms such as "aryloxy", refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The following heteroaryl groups are preferred:

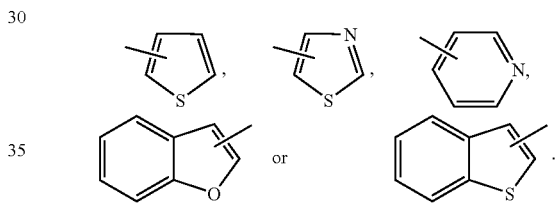

The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$ OC(O)alkyl, $C_1$-$C_6$ NHC(O)alkyl, C(O)OH, $C_1$-$C_6$ C(O)Oalkyl, C(O)NH$_2$, $C_1$-$C_6$ C(O)NHalkyl, $C_1$-$C_6$ C(O)N(alkyl)$_2$, —OCH$_2$CH$_2$—, —OCH$_2$CH$_2$CH$_2$—, —OCH$_2$O— or —OCH$_2$CH$_2$O— provided that the substituents are sterically compatible and the rules of chemical bonding and strain energy are satisfied. Preferred substituents include halogen, $C_1$-$C_2$ alkyl and $C_1$-$C_2$ haloalkyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily prepared utilizing standard procedures, see U.S. Pat. No. 6,297,197 B1.

Typical synthetic sequences by which 6-(1,1-difluoroalkyl)-pyridines of Formula I can be prepared are shown in Schemes 1 and 2:

Scheme 1

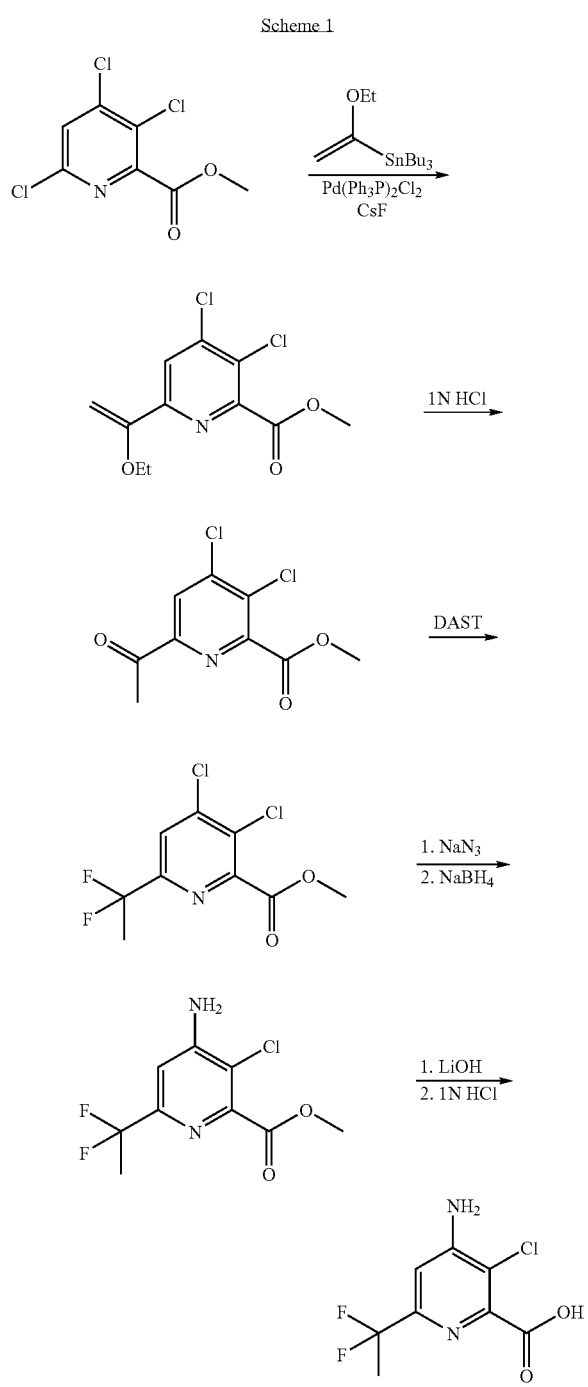

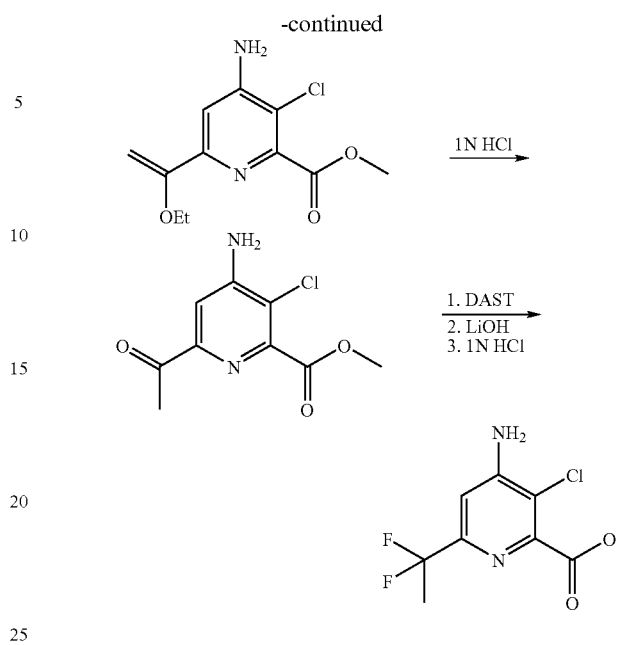

Reactions of alkoxyvinylorganotin compounds are well known as exemplified by the following references:

(1) Sato, Nobuhiro et. al., Synthesis (2001), (10), 1551-1555.

(2) Legros, J.-Y. et. al., Tetrahedron (2001), 57(13), 2507-2514.

(3) Guillier, F. et. al., Synthetic Communications (1996), 26(23), 4421-4436.

(4) Bracher, Franz; et. al., Liebigs Annalen der Chemie (1993), (8), 837-9.

Appropriate reactions such as difluorination of the carbonyl using typical fluorinating reagents, e.g., (diethylamino) sulfur trifluoride (DAST), provide the difluroalkyl group at the 6-position.

Appropriate reactions such as displacement of the corresponding 4-halopyridines with NaN₃, followed by reduction of the corresponding 4-azido derivatives provide an amino group at the 4-position.

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate. The imine or hydrazone can be prepared by reaction of the free amine or hydrazine with a suitable aldehyde or ketone.

Substituted 4-amino analogs can be prepared by reacting the corresponding 4-halopyridine-2-carboxylate or any other displaceable 4-substituent with the substituted amine.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or dichloromethane. The organic solvent and other volatiles can be removed by distillation or evaporation to obtain the desired compound of Formula I, which can be purified by standard procedures, such as by recrystallization or chromatography.

Scheme 2

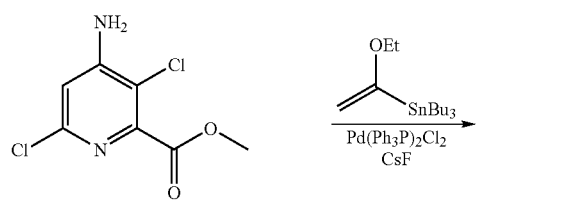

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of ways, power lines and any industrial areas where control of undesirable vegetation is desirable. Another use is the control of unwanted vegetation in crops such as wheat. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges. Use of the compounds to control undesirable vegetation in established crops is especially indicated. While each of the 6-(1,1-difluoroalkyl)-4-aminopicolinate compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 1 to about 2,000 g/Ha are generally employed in postemergence operations; for preemergence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, ima-zethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione. The herbicidal compounds of the present invention can, further, be used in conjunction with glyphosate and glufosinate on glyphosate-tolerant or glufosinate-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as cloquintocet, furilazole, dichlormid, benoxacor, mefenpyr-ethyl, fenclorazole-ethyl, flurazole, daimuron, dimepiperate, thiobencarb, fenclorim and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate and glufosinate tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin tolerant crops.

While it is possible to utilize the 6-(1,1-difluoroalkyl)-4-amino-picolinate compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims. The starting materials useful for the preparation of the compounds of the present invention, e.g., 3,4,6-trichloropyridine-2-carboxylic acid, are described in U.S. Pat. No. 6,297,197 B1.

EXAMPLES

1. Preparation of Methyl 6-acetyl-3,4-dichloropyridine-2-carboxylate

A solution of methyl 3,4,6-trichloropyridine-2-carboxylate (2.00 g, 8.31 mmol), ethoxyvinyltributyltin (3.09 mL, 9.15 mmol) and cesium fluoride (2.78 g, 18.30 mmol) in dioxane (50 mL) was sparged with nitrogen for 15 minutes. Dichlorobis(triphenylphosphine) palladium(II) (292 mg, 0.42 mmol) was then added and the mixture heated at 100° C. for 3 hours. After cooling, the mixture was concentrated, taken up into ethyl acetate and was filtered through a silica gel plug. The solvent was removed and the crude ethoxyvinyl intermediate was then dissolved in a solution of tetrahydrofuran (50 mL) and 1N HCl acid (20 mL). After stirring the mixture at room temperature overnight, the tetrahydrofuran was removed in vacuo and the remaining aqueous phase extracted with ethyl acetate. The organic layers were combined, dried ($MgSO_4$), and concentrated. Purification by column chromatography (10% ethyl acetate in hexane) provided methyl 3,4-dichloro-6-acetylpyridine-2-carboxylate (0.98 g, 3.95 mmol) as a white solid; $^1$H NMR ($CDCl_3$): δ 8.20 (s, 1H), 4.05 (s, 3H), 2.71 (s, 3H).

Similarly Prepared:

Methyl 6-acetyl-4-amino-3-chloropyridine-2-carboxylate; $^1$H NMR ($CDCl_3$): δ 7.06 (s, 1H), 6.95 (br.s, 2H), 1.90 (t, 3H).

2. Preparation of Methyl 3,4-dichloro-6-(1,1-difluoroethyl)pyridine-2-carboxylate (Diethylamino)sulfur trifluoride (DAST, 2.66 mL, 20 mmol) was added to a solution of methyl 6-acetyl-3,4-dichloropyridine-2-carboxylate (0.50 g, 2 mmol) in methylene chloride (25 mL). After stirring for 3 days at room temperature, the reaction mixture was poured into brine. The organic layer was separated and the aqueous phase extracted with dichloromethane. The organic layers were combined, dried ($MgSO_4$), and concentrated in vacuo. Purification by column chromatography (10% ethyl acetate in hexane) provided methyl 3,4-dichloro-6-(1,1-difluoroethyl)pyridine-2-carboxylate (0.36 g, 1.33 mmol) as a yellow liquid; $^1$H NMR ($CDCl_3$): δ 7.85 (s, 1H), 4.02 (s, 3H), 2.02 (t, d=18.7 Hz, 3H).

3. Preparation of Methyl 4-amino-3-chloro-6-(1,1-difluoroethyl)pyridine-2-carboxylate (Compound 1)

Sodium azide (26.5 mg, 0.41 mmol) was added to a solution of methyl 3,4-dichloro-6-(1,1-difluoroethyl)pyridine-2-carboxylate (100 mg, 0.37 mmol) in dimethylformamide (2 mL) and water (0.2 mL). After the reaction mixture was stirred at 50° C. for 5 hours, it was quenched with water and extracted with ethyl ether. The orgainc phase was dried and concentrated to provide the crude 4-azide compound. It was immediately taken up into methanol (2 mL) and sodium borohydride (21 mg, 0.55 mmol) was carefully added. After stirring for 10 minutes, water was added and the mixture concentrated. Ethyl acetate was added and the mixture washed with brine. The organic layer was dried ($MgSO_4$), filtered and concentrated to dryness. The crude product was purified by column chromatography (20% ethyl acetate in hexane) to give methyl 4-amino-3-chloro-6-(1,1-difluroethyl)pyridine-2-carboxylate (53 mg, 0.21 mmol) as an oil; $^1H$ NMR ($CDCl_3$): δ 7.04 (s, 1H), 4.92 (b.s, 2H), 3.98 (s, 3H), 1.97 (t, d=18.7 Hz, 3H).

4. Preparation of 4-amino-3-chloro-6-(1,1-difluoroethyl)pyridine-2-carboxylic acid (Compound 2)

A solution of lithium hydroxide (159 mg, 1.27 mmol) in water (6 mL) was added to a solution of methyl 4-amino-3-chloro-6-(1,1-difluroethyl)-pyridine-2-carboxylate (159 mg, 0.63 mmol) in tetrahydrofuran (6 mL). The mixture was vigorously stirred at room temperature overnight and was then concentrated to near dryness. After adding water, the reaction mixture was washed once with ethyl acetate to remove unreacted starting material. The aqueous layer was then acidified to pH<3 with 1N HCl and extracted with ethyl acetate. The organic layer was dried ($MgSO_4$), concentrated and the residue triturated with cold hexane to provide 4-amino-3-chloro-6-(1,1-difluoroethyl)-pyridine-2-carboxylic acid (105 mg, 0.44 mmol) as a white solid; $^1H$ NMR (DMSO-$d_6$): δ 7.02 (s, 1H), 6.94 (br.s, 2H), 1.90 (t, 3H).

Alternatively prepared from Methyl 6-acetyl-4-amino-3-chloropyridine-2-carboxylate:

(Diethylamino)sulfur trifluoride (2.66 mL, 20 mmol) was added to a solution of methyl 6-acetyl-4-amino-3-chloropyridine-2-carboxylate (0.50 g, 2.19 mmol) in methylene chloride (40 mL). After stirring for 3 days at room temperature, the reaction mixture was poured into brine. The organic layer was separated and the aqueous phase extracted with dichloromethane. The organic layers were combined, dried ($MgSO_4$), and concentrated in vacuo. Crude residue was dissolved in THF (25 mL) and a solution of LiOH (0.46 g, 10.9 mmol) in water added. After stirring overnight, half concentrated and washed once with EtOAc. Then aqueous acidified with sat citric acid. Extracted with EtOAc and dried to give the crude acid. Purified by prep HPLC (70% $CH_3CN$, rtime 3.5 mins) to provide 4-amino-3-chloro-6-(1,1-difluoroethyl)pyridine-2-carboxylic acid as a white solid acid, 238 mg (46% for the 2 steps).

5. Preparation of Herbicidal Compositions

In the following illustrative compositions, parts and percentages are by weight.

Emulsifiable Concentrations

| | WT % |
|---|---|
| Formulation A | |
| Compound 1 | 26.2 |
| Polyglycol 26-3 Nonionic emulsifier-(di-sec-butyl)-phenyl-poly(oxypropylene)block polymer with (oxyethylene). The polyoxyethelene content is about 12 moles. | 5.2 |

-continued

| | WT % |
|---|---|
| Witconate P12–20 (Anionic emulsifier-calcium dodecylbenzene sulfonate-60 wt. % active) | 5.2 |
| Aromatic 100 (Xylene range aromatic solvent) | 63.4 |
| Formulation B | |
| Compound 1 | 3.5 |
| Sunspray 11N (paraffin oil) | 40.0 |
| Polyglycol 26-3 | 19.0 |
| Oleic acid | 1.0 |
| Xylene range aromatic solvent | 36.5 |
| Formulation C | |
| Compound 1 | 13.2 |
| Stepon C-65 | 25.7 |
| Ethomeen T/25 | 7.7 |
| Ethomeen T/15 | 18.0 |
| Xylene range aromatic solvent | 35.4 |
| Formulation D | |
| Compound 1 | 30.0 |
| Agrimer Al-10 LC (emulsifier) | 3.0 |
| N-methyl-2-pyrrolidone | 67.0 |
| Formulation E | |
| Compound 1 | 10.0 |
| Agrimul 70-A (disperant) | 2.0 |
| Amsul DMAP 60 (thickener) | 2.0 |
| Emulsogen M (emulsifier) | 8.0 |
| Attagel 0 (suspension aid) | 2.0 |
| Crop oil | 76.0 |

These concentrates can be diluted with water to give emulsions of suitable concentrations for controlling weeds.

Wettable Powders

| | WT % |
|---|---|
| Formulation F | |
| Compound 2 | 26.0 |
| Polyglycol 26-3 | 2.0 |
| Polyfon H | 4.0 |
| Zeosyl 100 (Precipitated hydrated $SiO_2$) | 17.0 |
| Barden clay + inerts | 51.0 |
| Formulation G | |
| Compound 2 | 62.4 |
| Polyfon H (sodium salt of lignin sulfonate) | 6.0 |
| Sellogen HR (sodium naphthalene sulfonate) | 4.0 |
| Zeosyl 100 | 27.6 |
| Formulation H | |
| Compound 2 | 1.4 |
| Kunigel V1 (carrier) | 30.0 |
| Stepanol ME Dry (wetter) | 2.0 |
| Tosnanon GR 31 A | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules

Formulation I

| | WT % |
|---|---|
| Compound 2 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules

Formulation J

| | WT % |
|---|---|
| Compound 2 | 5.0 |
| Celetom MP-88 | 95.0 |

The active ingredient is applied in a polar solvent such as N-methyl-pyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

| | WT % |
|---|---|
| Compound 2 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids

Formulation L

| | WT % |
|---|---|
| Compound 2 | 3.67 |
| Monoethanolamine pH buffer | 0.5 |
| Water | 95.83 |

The active ingredient is dissolved in and appropiate amount of water and the additional monoethanolamine is added as a buffer. A water-soluble surfactant may be added. Other aids may be incorporated to improve physical, chemical and/or formulation properties.

6. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hr photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Table 1. Selectivity to wheat is shown in Table 2.

TABLE 1

| | | Post-emergent (% injury) | | | |
|---|---|---|---|---|---|
| Compound | Rate (ppm) | XANST | CHEAL | ECHCG | SETFA |
| 1 | 245 | 100 | 100 | 75 | 65 |
| 2 | 250 | 100 | 100 | 80 | 85 |

XANST = Cocklebur (*Xanthium strumarium*)
CHEAL = Lambsquarter (*Chenopodium album*)
ECHCG = Barnyardgrass (*Echinochloa crus-galli*)
SETFA = Giant Foxtail (*Setaria faberi*)

TABLE 2

| | | Post-emergent (% injury) | | |
|---|---|---|---|---|
| Compound | Rate | CHEAL | AMARE | TRZAS |
| 1 | 123 | 100 | 100 | 0 |

CHEAL = Lambsquarter (*Chenopodium album*)
AMARE = Pigweed (redroot) (*Amaranthus retroflexus*)
TRZAS = Wheat (var.*Merica*) (*Triticum aestivum*)

7. Evaluation of Preemergence Herbicidal Activity

Seeds of the desired test plant species were planted in a soil matrix prepared by mixing a loam soil (43 percent silt, 19 percent clay, and 38 percent sand, with a pH of about 8.1 and an organic matter content of about 1.5 percent) and sand in a 70 to 30 ratio. The soil matrix was contained in plastic pots with a surface area of 113 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 2 mL aliquots of the stock solution with 15 mL of the mixture and lower concentrations were prepared by serial dilution of the stock solution. A 2.5 mL aliquot of each solution of known concentration was sprayed evenly onto the soil surface (113 sq. cm) of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture.

The treated pots and control pots were placed in a greenhouse maintained with an approximate 15 hr photoperiod and temperatures of about 23-29° C. during the day and 22-28° C. during the night. Nutrients and water were added on a regular basis and supplemental lighting was provided with overhead metal halide 1000-Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination.

Some of the compounds tested, application rates employed, plant species tested, and results are given in Table 3.

TABLE 3

| | | Pre-emergent (% injury) | | | |
|---|---|---|---|---|---|
| Compound | Rate (ppm) | CHEAL | IPOHE | DIGSA | SETFA |
| 1 | 560 | 100 | 100 | 100 | 100 |
| 2 | 560 | 100 | 100 | 98 | 95 |

CHEAL = Lambsquarter (*Chenopodium album*)
IPOHE = Ivyleaf Morningglory (*Ipomoea hederacea*)
DIGSA = Crabgrass (large) (*Digitaria sanguinalis*)
SETFA = Giant Foxtail (*Setaria faberi*)

What is claimed is:

1. A compound of the formula I

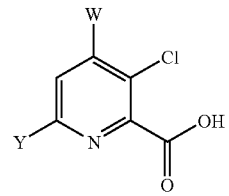

wherein
Y represents $-CF_2(C_1-C_3$ alkyl); and
W represents $-NO_2$, $-N_3$, $-NR_1R_2$, $-N=CR_3R_4$ or $-NHN=CR_3R_4$ wherein
$R_1$ and $R_2$ independently represent H, $C_1-C_6$ alkyl, $C_3-C_6$ alkenyl, $C_3-C_6$ alkynyl, aryl, heteroaryl, hydroxy, $C_1-C_6$ alkoxy, amino, $C_1-C_6$ acyl, $C_1-C_6$ carboalkoxy, $C_1-C_6$ alkylcarbamyl, $C_1-C_6$ alkylsulfonyl, $C_1-C_6$ trialkylsilyl or $C_1-C_6$ dialkyl phosphonyl or $R_1$ and $R_2$ taken together with N represent a 5- or 6-membered saturated or unsaturated ring which may contain additional O, S or N heteroatoms; and $R_3$ and $R_4$ independently represent H, $C_1-C_6$ alkyl, $C_3-C_6$ alkenyl, $C_3-C_6$ alkynyl, aryl or heteroaryl or $R_3$ and $R_4$ taken together with =C represent a 5- or 6-membered saturated ring; and agriculturally acceptable derivatives of the carboxylic acid group.

2. The compounds of claim 1 in which Y represents $-CF_2CH_3$.

3. The compounds of claim 1 in which W represents $-NR_1R_2$ where $R_1$ and $R_2$ independently represent H or $C_1-C_6$ alkyl.

4. The compound of claim 1 in which Y represents $-CF_2CH_3$ and W represents $-NH_2$.

5. A herbicidal composition comprising a herbicidally effective amount of a compound of Formula I, as claimed in claim 1, in admixture with an agriculturally acceptable adjuvant or carrier.

6. A method of controlling undesirable vegetation which comprises contacting the vegetation or the locus thereof with or applying to the soil to prevent the emergence of vegetation an herbicidally effective amount of a compound of Formula I, as claimed in claim 1.

* * * * *